United States Patent [19]

Harandi et al.

[11] Patent Number: 5,026,529

[45] Date of Patent: Jun. 25, 1991

[54] PRODUCTION OF ETHERS FROM METHANOL

[75] Inventors: Mohsen N. Harandi, Lawrenceville; Hartley Owen, Belle Mead, both of N.J.

[73] Assignee: Mobil Oil Corporation, New York, N.Y.

[21] Appl. No.: 297,731

[22] Filed: Jan. 17, 1989

Related U.S. Application Data

[63] Continuation-in-part of Ser. No. 124,525, Nov. 24, 1987, Pat. No. 4,831,195.

[51] Int. Cl.$^5$ .............................................. B01J 8/00
[52] U.S. Cl. .................................... 422/190; 422/256; 568/697; 555/304; 555/310
[58] Field of Search ............... 422/190, 256; 568/697; 585/310, 319, 322, 301, 304

[56] References Cited

U.S. PATENT DOCUMENTS 4,827,045  5/1989  Harandi et al. ..................... 568/697
4,827,046  5/1989  Harandi et al. ..................... 568/697

Primary Examiner—Robert J. Warden
Assistant Examiner—Amalia L. Santiago
Attorney, Agent, or Firm—Alexander J. McKillop; Charles J. Speciale; L. G. Wise

[57] ABSTRACT

Improved operating techniques and apparatus for converting methanol or the like to intermediate olefins and etherification products, such as methyl t-butyl ether, by extracting crude methanol feedstock with an olefinic liquid hydrocarbon stream containing $C_4^+$ iso-olefins. The methanol extract phase is reacted under etherification conditions. The aqueous methanol raffinate stream is converted catalytically to olefins for recovery of $C_4^+$ olefinic liquid hydrocarbons useful as extraction solvent.

A continuous system is provided for converting crude aqueous alcohol feedstock to olefinic hydrocarbons and octane enhancing ethers comprising: extractor means for contacting feedstock liquid containing water with a liquid hydrocarbon extraction stream to provide an extract liquid stream rich in alcohol and an aqueous raffinate stream lean in alcohol; catalytic reactor means for contacting the aqueous alcohol raffinate stream in a catalytic reaction zone with a crystalline acid zeolite catalyst at elevated temperature in an intermediate olefins production zone under process conditions to convert a major portion of alcohol to hydrocarbons; separation means to recover a gaseous stream rich in $C_3^-$ hyrocarbons and a liquid stream comprising $C_4^+$ hydrocarbons; recycle means for contacting at least a portion of the liquid hydrocarbon stream from said separation means with crude alcohol feedstock in said extractor means; and etherification reactor means for contacting at least a portion of extracted alcohol and olefinic liquid hydrocarbon with etherification catalyst to produce an ether product stream.

3 Claims, 1 Drawing Sheet

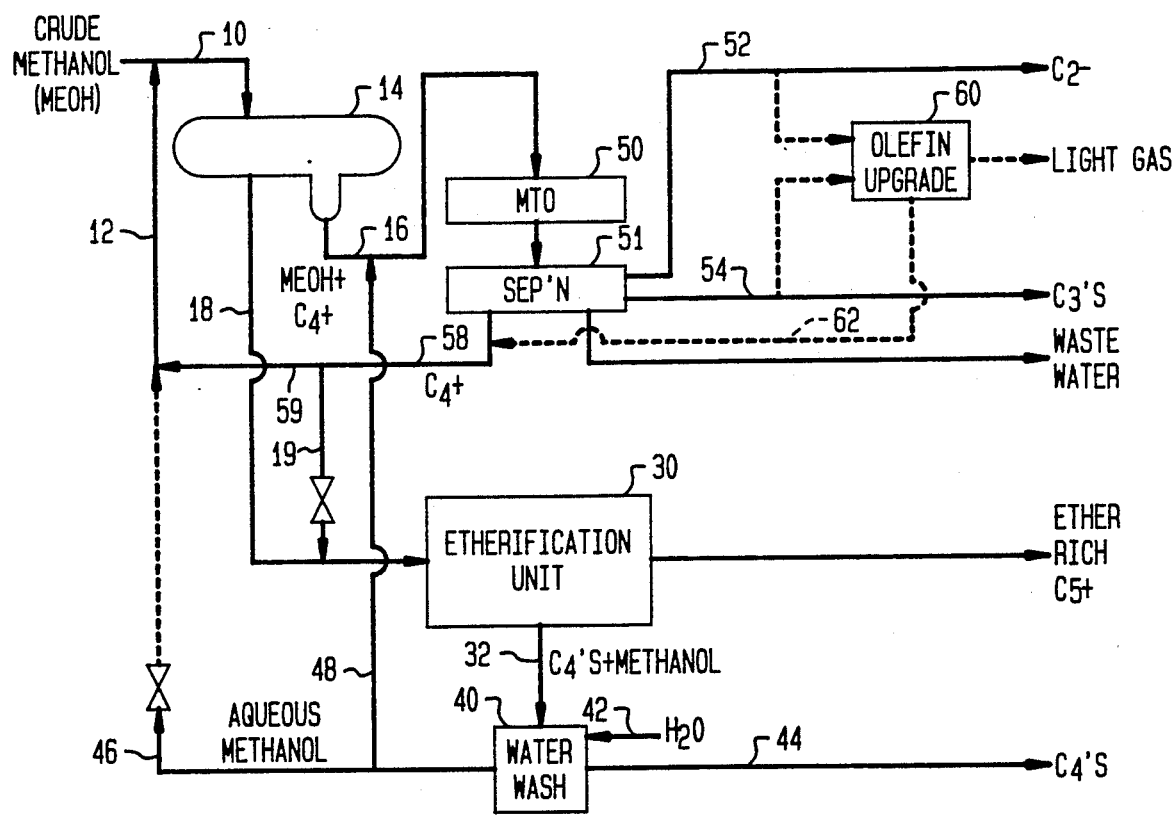
FIG.

PRODUCTION OF ETHERS FROM METHANOL

REFERENCE TO COPENDING APPLICATIONS

This application is a continuation-in-part of U.S. Patent Application Ser. No. 124,525, filed 24 Nov. 1987, incorporated herein by reference, now U.S. Pat. No. 4,831,195.

BACKGROUND OF THE INVENTION

This invention relates to techniques for converting alcohol feedstocks, such as crude methanol or the like, to lower ether products, eg-methyl tertiary-alkyl ethers. This invention also provides a unique reactor and recovery system for converting methanol to lower olefins. In particular, it provides a continuous system for producing an intermediate olefinic product rich in $C_2$-$C_5$ alkenes. In view of the availability and low cost of synthetic methanol (MeOH), primary emphasis is placed on this feedstock material in following description of the methanol-to-olefin (MTO) process.

In its broader aspects, this invention relates to an integrated system for converting crude methanol to valuable products by etherifying lower branched olefins, such as $C_4$-$C_5$ isoolefins. It is known that isobutylene may be reacted with methanol over an acidic catalyst to provide methyl tertiary butyl ether (MTBE) and isoamylenes may be reacted with methanol over an acidic catalyst to produce tertiary-amyl methyl ether (TAME). The etherification catalyst employed is preferably an ion exchange resin in the hydrogen form. Substantially any acidic catalyst may be employed with varying degrees of success. That is, acidic solid catalysts may be used; such as, sulfonic resins, phosphoric acid modified kieselguhr, silica alumina and acid zeolites. Those ethers having the formula $CH_3$—O—R, where R is an isoalkyl radical, are particularly useful as octane improvers for liquid fuels, especially gasoline.

Increasing demand for high octane gasolines blended with lower aliphatic alkyl ethers as octane boosters and supplementary fuels has created a significant demand for isoalkylethers, especially the $C_5$ to $C_7$ methyl alkyl ethers, such as methyl tertiary butyl ether (MTBE) and tertiary amyl methyl ether (TAME). Methanol may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contains a significant amount of water, usually in the range of 4 to 20 wt%; however, the present invention is useful for removing water in lesser amounts or greater.

Processes for converting lower oxygenates such as methanol to hydrocarbons are known (eg-methanol-to-olefins -MTO), and have become of great interest in recent times because they offer an attractive way of producing liquid hydrocarbon fuels, especially gasoline, from sources which are not of liquid petroleum origin. In particular, they provide a way by which methanol can be converted to a major amount of $C_2$-$C_5$ olefins and a minor amount of gasoline boiling range products in good yields.

It is main object of the present invention to provide a novel and economic technique for removing excess water from crude methanol feedstocks, including novel operating methods and equipment for treating these oxygenate feedstocks prior to conversion to olefins and etherification.

SUMMARY OF THE INVENTION

A continuous technique has been found for converting crude methanol to methyl t-alkyl ethers in a catalytic reactor system with acid etherification catalyst comprising:

(a) extraction means for contacting a crude methanol feedstock containing a minor amount of water with a liquid hydrocarbon extraction stream rich in $C_4$+ iso-olefinic hydrocarbons under extraction conditions favorable to selective extraction of the methanol, thereby providing an extract liquid stream rich in methanol and an aqueous raffinate stream containing unextracted methanol;

(b) first reactor means including means for charging the extract liquid stream with $C_4$+ olefinic hydrocarbon and extracted methanol substantially free of water to a catalytic etherification reaction zone under process conditions for converting methanol and iso-olefin to predominantly methyl tertiary-alkyl ether;

(c) second catalytic reactor means for catalytically converting the aqueous raffinate stream in contact with methanol-to-olefin catalyst to produce a mixture of $C_2$-$C_5$ or heavier olefins, including $C_4$+ iso-olefinic component;

(d) washing means for contacting at least a portion of etherification reaction effluent from step (b) with water to recover methanol from the effluent; and (e) means for recovering a product stream rich in methyl tert-alkyl ether.

These and other objects and features of the invention will be understood from the following description and in the drawing.

DRAWING

The single FIGURE of the drawing is a schematic olefins production and etherification process flowsheet depicting the present invention.

DETAILED DESCRIPTION

The crude methanol commercially available from syngas processes may contain, for instance 4 to 17 wt% water, which must be removed, preferably to a methanol purity of about 99.8 wt%. It has been found that more than 75% of crude feedstock methanol can be recovered by liquid extraction with light olefinic liquid extractant, such as butenes and $C_5$+ light olefinic naphtha. The typical feed ratio range is about 5 to 20 parts hydrocarbon extractant per part by volume of methanol.

Referring to the drawing, a continuous stream of crude methanol (MeOH) feedstock is introduced via conduit 10 with a stream of hydrocarbon liquid extractant and optional recycle introduced via conduit 12 to an inlet of extraction separation unit 14. These streams are contacted under liquid extraction conditions to provide an aqueous raffinate phase. An aqueous stream containing a major amount of the water present in the crude feedstock is withdrawn via conduit 16. The lighter organic extract phase containing hydrocarbon extraction solvent and extracted methanol is recovered from extraction unit 12 via conduit 18, combined with additional $C_4$+ olefins from line 19 and introduced under temperature and process conditions suitable for conversion of methanol in contact with etherification catalyst in etherification reactor system 30, including a conventional reactor unit and effluent distillation unit. From reactor system 30 a first effluent stream containing unreacted methanol and $C_4^-$ light hydrocarbons leaves via line 32 and is passed to effluent washer vessel 40, where it is contacted with wash water introduced via line 42 for extraction of unreacted methanol from first light hydrocarbon product stream 44, rich in unreacted butylenes. The aqueous raffinate stream 16 consists essentially of water, partititioned methanol and a minor amount of hydrocarbon. The aqueous raffinate containing unextracted oxygenate is passed to a MTO reaction zone 50 under process conditions to convert oxygenate to predominantly olefinic hydrocarbons. This is followed by separating MTO reaction effluent to recover aqueous liquids byproduct, gas rich in $C_3^-$ hydrocarbons, and an intermediate liquid product stream comprising $C_4^+$ hydrocarbons. The raffinate methanol is converted to a mixture of olefins in the MTO system, including a second catalytic reactor means 50 and effluent separation means 51. The separation unit comprises a conventional fractionation unit to provide light hydrocarbon product streams 52, 54 and recovers byproduct water effluent stream 56 and liquid intermediate olefins stream 58, rich in $C_4^+$ olefin isomers. Optionally, light olefinic MTO effluent containing ethene, propene, etc., may be further upgraded in reactor system 60 to supplement the liquid $C_4^+$ stream 58 with additional $C_4$-$C_7$ olefins for instance from conduit 62. The combined liquid stream 58 is apportioned according to process demand between etherification feedstream 19 and extraction solvent stream 59, which may be combined with a portion of recycled wet methanol from wash unit 40 via conduit 46.

EXTRACTION UNIT OPERATION

The typical preferred crude feedstock material is methanol containing about 4 to 17% by weight water. The extraction contact unit may be a stirred multi-stage vertical extraction column adapted for continuous operation at elevated pressure. Any suitable extraction equipment may be employed, including cocurrent, cross-current or single contactors, wherein the liquid methanol feedstock is intimately contacted with a substantially immiscible liquid hydrocarbon solvent, which may be a mixture of $C_4^+$ aliphatic components including lower alkanes, n-alkenes or relatively pure isoalkenes, such as isobutylene, etc. This unit operation is described in *Kirk-Othmer Encyclopedia of Chemical Technology* (Third Ed.), 1980, pp. 672-721. Other equipment for extraction is disclosed in U.S. Pat. No. 4,349,415 (DeFilipi et al) and U.S. Pat. No. 4,626,415 (Tabak). The methanol extraction step can be performed advantageously in a countercurrent multistage design, such as a simple packed column, rotating disk column, agitated column with baffles or mesh, or a series of single stage mixers and settlers.

ETHERIFICATION OPERATION

The reaction of methanol with isobutylene and isoamylenes at moderate conditions with a resin catalyst is known technology, as provided by R. W. Reynolds, et al., *The Oil and Gas Journal*, June 16, 1975, and S. Pecci and T. Floris, *Hydrocarbon Processing*, December 1977. An article entitled "MTBE and TAME—A Good Octane Boosting Combo", by J. D. Chase, et al., *The Oil and Gas Journal*, Apr. 9, 1979, pages 149-152, discusses the technology. A preferred catalyst is a trifunctional ion exchange resin which etherifies, hydrogenates and isomarizes the reactant streams. A typical acid catalyst is Amberlyst 15 sulfonic acid resin.

MTBE and TAME are known to be high octane ethers. The article by J. D. Chase, et al., *Oil and Gas Journal*, Apr. 9, 1979, discusses the advantages one can achieve by using these materials to enhance gasoline octane. The octane blending number of MTBE when 10% is added to a base fuel ($R+O=91$) is about 120. For a fuel with a low motor rating ($M+O=83$) octane, the blending value of MTBE at the 10% level is about 103. On the other hand, for an ($R+O$) of 95 octane fuel, the blending value of 10% MTBE is about 114.

MTO REACTOR SYSTEM

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

Catalyst versatility permits the same zeolite to be used in both methanol dehydration and olefin formation. While it is within the inventive concept to employ substantially different catalysts in plural stages, it is advantageous to a standard ZSM-5 having a silica alumina molar ratio of 70:1 or greater in a once-through fluidized bed unit to convert feedstock oxygenate to hydrocarbons.

The MTO catalysts preferred for use herein include the crystalline aluminosilicate zeolites having a silica to alumina ratio of at least 12, a constraint index of about 1 to 12. Representative of the ZSM-5 type zeolites are ZSM-5, ZSM-11, ZSM-12, ZSM-22, ZSM-23, ZSM-35 and ZSM-48. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,979. Also, see U.S. Pat. No. 3,832,449 for ZSM-12; U.S. Pat. No. 4,076,842 for ZSM-23; U.S. Pat. No. 4,016,245 for ZSM-35; and U.S. Pat. No. 4,375,573 for ZSM-48. The disclosures of all patents cited herein are incorporated herein by reference. The medium pore shape selective catalysts are sometimes known as porotectosilicates or "pentasil" catalysts, and may have a pore size of about 5 to 7 Angstroms. In addition to the preferred aluminosilicates, silicoaluminophosphate, gallosilicate, borosilicate, ferrosilicate and "silicalite" materials may be employed.

Various zeolitic catalysts are useful for converting methanol and other lower aliphatic alcohols or corresponding ethers to olefins. Recent interest has been directed to a catalytic process for converting methanol over ZSM-5 and related catalysts to valuable hydrocarbons rich in ethene and $C_3^+$ alkenes. Various processes are described in U.S. Pat. No. 3,894,107 (Butter et al); U.S. Pat. Nos. 3,928,483; 4,025,575; 4,252,479 (Chang et al); U.S. Pat. No. 4,025,572 (Lago); U.S. Pat. No. 4,328,384 (Daviduk et al); and U.S. Pat. No. 4,547,616

(Avidan et al); incorporated herein by reference. It is generally known that MTO processes can be optimized to produce a major fraction of $C_2$–$C_4$ olefins; however, a significant $C_5+$ byproduct may be coproduced. Prior process techniques for increasing lower olefin selectivity have provided for controlled deposition of coke byproduct on the catalyst surface.

Methanol may be first subjected to a dehydrating step, using a catalyst such as gamma-alumina, to form an equilibrium mixture of methanol, dimethyl ether (DME) and water. This mixture is then passed at elevated temperature and pressure over a catalyst such as ZSM-5 zeolite for conversion to the hydrocarbon products. Water may be removed from the methanol dehydration products prior to further conversion to hydrocarbons and the methanol can be recycled to the dehydration step, as described in U.S. Pat. No. 4,035,430. Removal of the water is desirable because the catalyst may tend to become deactivated by the presence of excess water vapor at the reaction temperatures employed; but this step is not essential.

ZSM-5 type pentasil zeolites are particularly useful in the MTO process because of their regenerability, long life and stability under the extreme conditions of MTO operations. Usually the zeolite crystals have a crystal size from about 0.02 to 2 microns or more, with large crystals on the order of 0.1–1 micron being preferred. In order to obtain the desired particle size for fluidization in the turbulent regime, the zeolite catalyst crystals are bound with a suitable inorganic oxide, such as silica, alumina, etc. to provide a zeolite concentration of about 5 to 90 wt. %. It is advantageous to employ a particle size range consisting essentially of 1 to 150 microns. Average particle size is usually about 20 to 100 microns, preferably 40 to 80 microns. The catalyst in the fluidized bed reactor is maintained at an average acid cracking activity (alpha value) of about 1 to 15, preferably about 3 to 8, on a coke-free basis. The average coke content is less than 15 weight percent, preferably about 5–10 wt. % of the clean-burned catalyst. By controlling the catalytic properties of the system, the selectivity to produce $C_2$–$C_5$ olefins can be enhanced.

In a preferred embodiment, aqueous methanol raffinate 16 is passed to the MTO reactor system 50 with wet methanol wash stream 48 (optional recycle). The combined feedstock and recycle is conducted at a temperature of about 275°–525° C., preferrably about 475°–500° C., and a pressure of about 100–1000 kPa to the MTO catalytic reactor. Effluent from the reaction zone is passed to a separation zone for recovery of light gas streams 52,54, byproduct water and a liquid hydrocarbon stream 58 containing a mixture of butenes, isobutylene, pentenes, isoamylene, and $C_6+$ gasoline range aromatics and aliphatics. It may be desirable to upgrade $C_2$–$C_3$ lower olefins (see U.S. Pat. No. 4,579,999, Gould et al) in an optional intermediate stage reactor system 60, with recovery of $C_3-$ light offgas and an upgraded olefinic hydrocarbon stream 62 containing etherifiable isoolefins, such as isobutylene and isoamylene.

The present invention is particularly advantageous in the economic dewatering of crude methanol, thus avoiding expensive and energy-intensive prefractionation by distillation. Various modifications can be made to the system, especially in the choice of equipment and non-critical processing steps. While the invention has been described by specific examples, there is no intent to limit the inventive concept as set forth in the following claims.

What is claimed is:

1. A continuous catalytic reactor system for converting crude methanol to methyl t-alkyl ethers comprising:
    (a) extraction means for contacting a crude methanol feedstock containing a minor amount of water with a liquid hydrocarbon extraction stream rich in $C_4+$ iso-olefinic hydrocarbons under extraction conditions favorable to selective extraction of the methanol, thereby providing an extract liquid stream rich in methanol and an aqueous raffinate stream containing unextracted methanol;
    (b) first etherification reactor means including means for charging the extract liquid stream with $C_4+$ olefinic hydrocarbon and extracted methanol substantially free of water to a catalytic etherification reaction zone in contact with acid etherification catalyst under process conditions for converting methanol and iso-olefin to predominantly methyl tertiary-alkyl ether;
    (c) second catalytic reactor means for catalytically converting the aqueous raffinate stream in contact with methanol-to-olefin catalyst to produce a hydrocarbon mixture containing $C_2$–$C_5$ olefins, including $C_4+$ iso-olefinic component;
    (d) washing means for contacting at least a portion of etherification reaction effluent from step (b) with water to recover methanol from the effluent; and
    (e) means for recovering from the second reactor means a product stream rich in methyl tert-alkyl ether.

2. The reactor system of claim 1 further comprising effluent separation means for recovering from second catalytic reactor effluent an aqueous liquid byproduct stream, a gaseous stream rich in $C_3-$ hydrocarbons and an olefinic liquid hydrocarbon stream comprising $C_4+$ hydrocarbons; and
    recycle means for contacting at least a portion of said olefinic liquid hydrocarbon stream from said separation means with crude alcohol feedstock in said extractor means.

3. The reactor system of claim 1 wherein the methanol-to-olefin catalyst consists essentially of aluminosilicate zeolite having the structure of HZSM-5.